US009862949B2

(12) United States Patent
Dimmeler et al.

(10) Patent No.: US 9,862,949 B2
(45) Date of Patent: Jan. 9, 2018

(54) METHOD FOR THE INHIBITION OF ANGIOGENESIS

(71) Applicant: t2cure GmbH, Frankfurt am Main (DE)

(72) Inventors: Stefanie Dimmeler, Frankfurt (DE); Andreas M. Zeiher, Frankfurt (DE); Angelika Bonauer, Frankfurt (DE); Carmen Urbich, Duesseldorf (DE)

(73) Assignee: T2CURE GMBH, Frankfurt am Main (DE)

( * ) Notice: Subject to any disclaimer, the term of this patent is extended or adjusted under 35 U.S.C. 154(b) by 0 days.

(21) Appl. No.: 15/040,487

(22) Filed: Feb. 10, 2016

(65) Prior Publication Data

US 2016/0237433 A1    Aug. 18, 2016

Related U.S. Application Data

(63) Continuation of application No. 14/448,119, filed on Jul. 31, 2014, now Pat. No. 9,279,123, which is a continuation of application No. 13/569,786, filed on Aug. 8, 2012, now Pat. No. 8,912,158, which is a continuation of application No. 12/739,876, filed as application No. PCT/DE2008/001759 on Oct. 30, 2008, now Pat. No. 8,258,113.

(30) Foreign Application Priority Data

Oct. 30, 2007    (DE) .................. 10 2007 052 114

(51) Int. Cl.
| | |
|---|---|
| *C12N 15/11* | (2006.01) |
| *C12Q 1/68* | (2006.01) |
| *C12N 15/113* | (2010.01) |
| *A61K 31/7088* | (2006.01) |
| *C07H 21/02* | (2006.01) |

(52) U.S. Cl.
CPC ........ *C12N 15/113* (2013.01); *A61K 31/7088* (2013.01); *C12N 2310/113* (2013.01); *C12N 2320/50* (2013.01)

(58) Field of Classification Search
CPC ................ C12N 15/111; C12N 15/113; C12N 2310/141; C12Q 1/6883; C12Q 2600/178; C12Q 2600/136
See application file for complete search history.

(56) References Cited

U.S. PATENT DOCUMENTS

| | | |
|---|---|---|
| 2005/0261218 A1 | 11/2005 | Esau et al. |
| 2008/0026951 A1 | 1/2008 | Brown et al. |
| 2010/0184821 A1 | 7/2010 | Mendell et al. |
| 2010/0257618 A1 | 10/2010 | Croce et al. |
| 2010/0267804 A1 | 10/2010 | Port et al. |

FOREIGN PATENT DOCUMENTS

| | | |
|---|---|---|
| DE | 10 2007 052 114 A1 | 5/2009 |
| WO | WO 2006/133022 A2 | 12/2006 |
| WO | WO 2008/014008 A2 | 1/2008 |
| WO | WO 2008/070082 A2 | 6/2008 |
| WO | WO 2009/004632 A2 | 1/2009 |
| WO | WO 2009/012468 A2 | 1/2009 |

OTHER PUBLICATIONS

Tsuchida et al., miR-92 is a key oncogenic component of the miR-17-92 cluster in colon cancer, 2011, Cancer Science, vol. 102, pp. 2264-2271.*
Zhang et al., MicroRNA-92a functions as an oncogene in colorectal cancer by targeting PTEN, 2014, Digestive Diseases and Sciences, vol. 59, pp. 98-107.*
Lei et al., Inhibition of miR-92b suppresses nonsmall cell lung cancer cells growth and motility by targeting RECK, 2014, Molecular and Cellular Biochemistry, vol. 387, pp. 171-176.*
Wu et al., Argonaute 2 promotes myeloma angiogenesis via microRNA dysregulation, 2014, Journal of Hematology & Oncology, vol. 7:40, pp. 1-14.*
Lin et al., STAT3 upregulates miR-92a to inhibit RECK expression and to promote invasiveness of lung cancer cells, 2013, British Journal of Cancer, vol. 109, pp. 731-738.*
Zhou et al., miR-92a is upregulated in cervical cancer and promotes cell proliferation and invasion by targeting FBXW7, 2015, BBRC, vol. 458, pp. 63-69.*
Chen et al., microRNA-92a promotes lymph node metastasis of human esophageal squamous cell carcinoma via E-cadherin, 2011, JBC, vol. 286, pp. 10725-10734.*
Ren et al., MicroRNA-92a promotes growth, metastasis, and chemoresistance in non-small cell lung cancer cells by targeting PTEN, 2016, Tumor Biology, vol. 37, pp. 3215-3225.*
Umezu et al., Leukemia cell to endothelial cell communication via exosomal miRNAs, 2013, Oncogene, vol. 32, pp. 2747-2755.*
Bonauer, Angelika et al. "MicroRNA-92a Controls Angiogenesis and Functional Recovery of Ischemic Tissues in Mice," *Science*, Jun. 26, 2009, 324:1710-1713.
Database EMBL, Accession No. AB176708, May 10, 2004, XP-002339404.
Davis, Scott et al., "Potent inhibition of microRNA in vivo without degradation," *Nucleic Acids Research*, 2009, 37(1):70-77.
Dews, Michael et al., "Augmentation of tumor angiogenesis by a Myc-activated microRNA cluster," *Nature Genetics*, Sep. 2006, 38(9):1060-1065.

(Continued)

*Primary Examiner* — Dana Shin
(74) *Attorney, Agent, or Firm* — Saliwanchik, Lloyd & Eisenschenk

(57) ABSTRACT

The invention relates to a method for influencing the miR-92 expression in a cell, comprising the following steps: (a) providing a cell; and (b1) reducing the miR-92 expression in the cell in order to promote the vascularization or vessel repair by introducing an antisense molecule against miR-92 into the cell, or (b2) increasing the miR-92 expression in the cell for an inhibition of the tumor angiogenesis by introducing a construct into the cell, wherein said construct includes an expressible miR-92 sequence. Furthermore, the invention relates to a pharmaceutical composition, comprising an agent for reducing the miR-92 activity or expression in a cell in the form of an antisense molecule against miR-92, or an agent for increasing the miR-92 expression in a cell in the form of a construct for expressing miR-92.

2 Claims, 13 Drawing Sheets

(56) References Cited

OTHER PUBLICATIONS

Hammond, Scott M., "MicroRNA therapeutics: a new niche for antisense nucleic acids," *TRENDS in Molecular Medicine*, Mar. 2006, 12(3):99-101.
Hinkel, Rabea et al., "Inhibition of MicroRNA-92a Protects Against Ischemia-Reperfusion Injury in a Large Animal Model," *Circulation*, Jul. 29, 2013, 128(10):1066-1075.
Kuebacher, Angelika et al., "Abstract 5442: MicroRNA 92a Controls Vessel Growth and Functional Recovery After Ischemia," *Circulation*, 2008, 118: S_550.
Kuehbacher, A. et al. "Abstract 896: Identification of Pro- and Anti-angiogenic MicroRNAs," *Circulation*, Oct. 16, 2007, 16(6):Abstract.
Kuehbacher, Angelika et al., "Role of dicer and drosha for endothelial microRNA expression and angiogenesis," *Circulation Research*, Jul. 6, 2007, 101(6):59-68.
Kuehbacher, Angelika et al., "Targeting microRNA expression to regulate angiogenesis," *TRENDS in Pharmacological Sciences*, Dec. 18, 2007, 29(1):12-15.
Krützfeldt, Jan et al., "Silencing of microRNAs in vivo with 'antagomirs'," *Nature*, Dec. 2005, 438:685-689.
Kuhlencordt, Peter J. et al. "Accelerated Atherosclerosis, Aortic Aneurysm Formation, and Ischemic Heart Disease in Apolipoprotein E/Endothelial Nitric Oxide Synthase Double-Knockout Mice," *Circulation*, Jul. 24, 2001, pp. 448-454.
Loyer, Xavier et al., "Inhibition of microRNA-92a Prevents Endothelial Dysfunction and Atherosclerosis in Mice," *Circulation Research*, Nov. 19, 2013, pp. 1-30.
Reed, Dwayne et al. "Are Aortic Aneurysms Caused by Atherosclerosis?" *Circulation*, Jan. 1992, 85(1):205-211.
Venturini, Letizia et al., "Expression of the miR-17-92 polycistron in chronic myeloid leukemia (CML) CD34+ cells," *Blood*, May 15, 2007, 109(10):4399-4405.
Weiler, J. et al., "Anti-miRNA oligonucleotides (AMOs): ammunition to target miRNAs implicated in human disease?," *Gene Therapy*, 2006, 13:496-502.
Aicher, A. et al., "Essential role of endothelial nitric oxide synthase for mobilization of stem and progenitor cells." Nature Medicine, Nov. 2003, 9(11): 1370-1376.
Auerbach, R. et al., "Angiogenesis Assays: A Critical Overview." Clinical Chemistry, 2003, 49(1): 32-40.
Doebele, C. et al., "Members of the microRNA-17-92 cluster exhibit a cell-intrinsic antiangiogenic function in endothelial cells." Blood, Jun. 2010, 115(23): 4944-4950.
Heiss, M. et al., "Endothelial cell spheroids as a versatile tool to study angiogenesis in vitro." The FASEB Journal, Apr. 2015, 29(7): 3076-3084.
Kim, S. et al., "Regulation of Integrin avB3-mediated Endothelial Cell Migration and Angiogenesis by Integrin a5B1 and Protein Kinase A*." J. Biol. Chem., Aug. 2000, 275(43): 33920-33928.
Potente, M. et al., "SIRT1 controls endothelial angiogenic functions during vascular growth." Genes & Development, 2007, 21: 2644-2658.
Staton, C. A. et al., "Current methods for assaying angiogenesis in vitro and in vivo." Int. J. Exp. Path., Jul. 2004, 85: 233-248.
Awata, T., "Molecular genetics of Diabetes ocular complications (retinopathy,maculopathy)." Journal—Japan Diabetes Society, 2005, 48 (10): Introduction.
Kuebacher, Angelika et al., "Abstract 5443: MicroRNA 92a Controls Vessel Growth and Functional Recovery After Ischemia," Circulation, 2008, 118S_550.
Lee, Y. K. et al., "Elevated HIF-1α Levels in CLL B Cells May Explain Their Autocrine VEGF Secretion." Blood, 2006, 108 (11): Abstract.
The American Association for the Study of Liver Diseases, "AASLD Abstracts." Hepatology, Oct. 2007, 46 (Supplement S1): 530A-531A.

\* cited by examiner

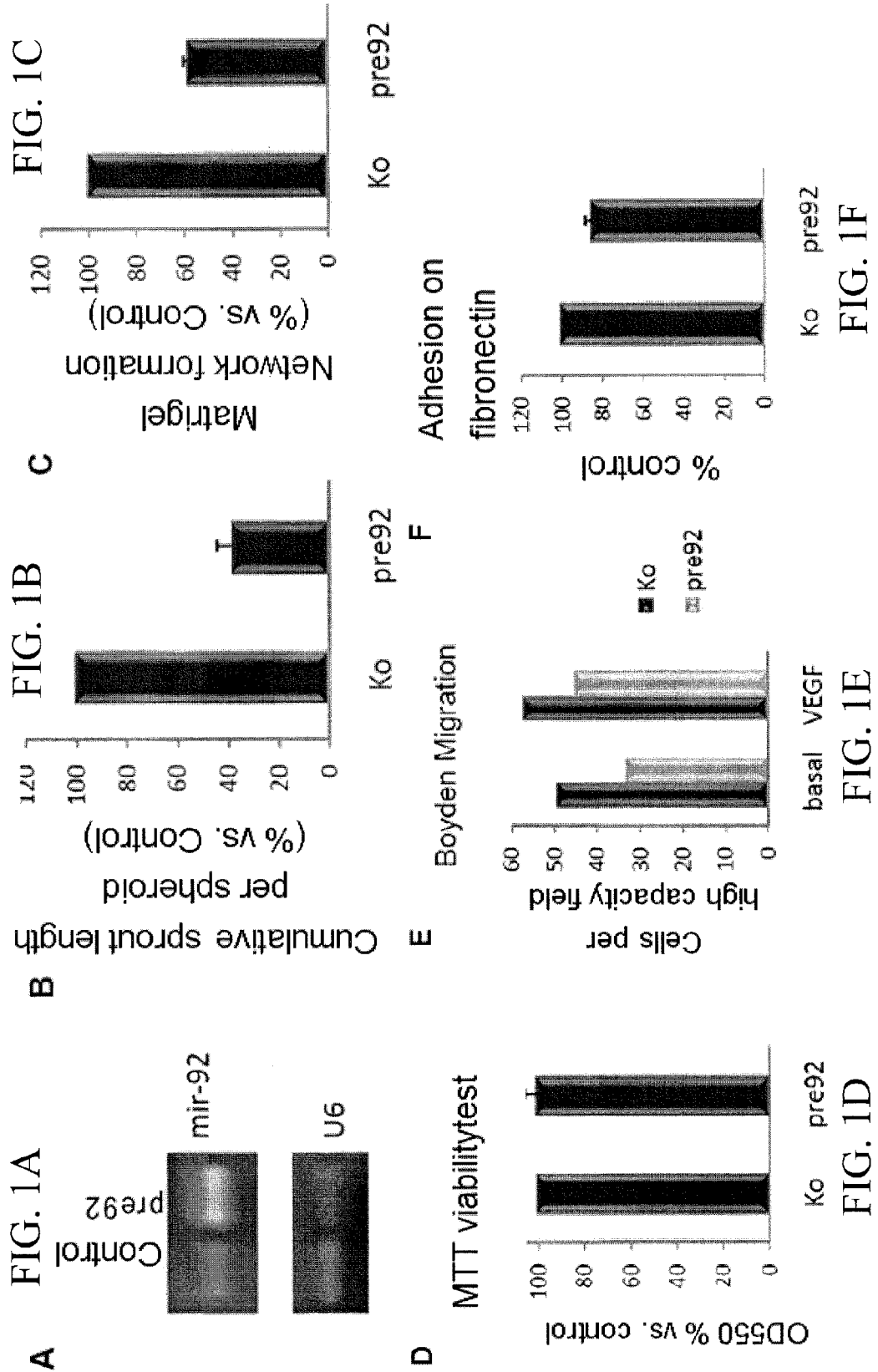

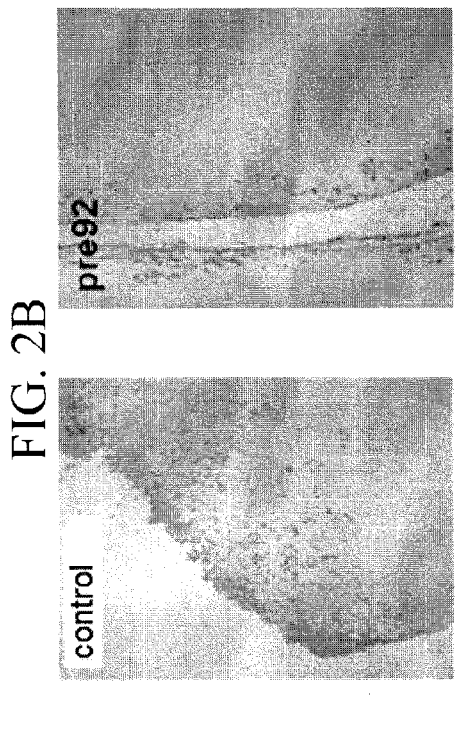
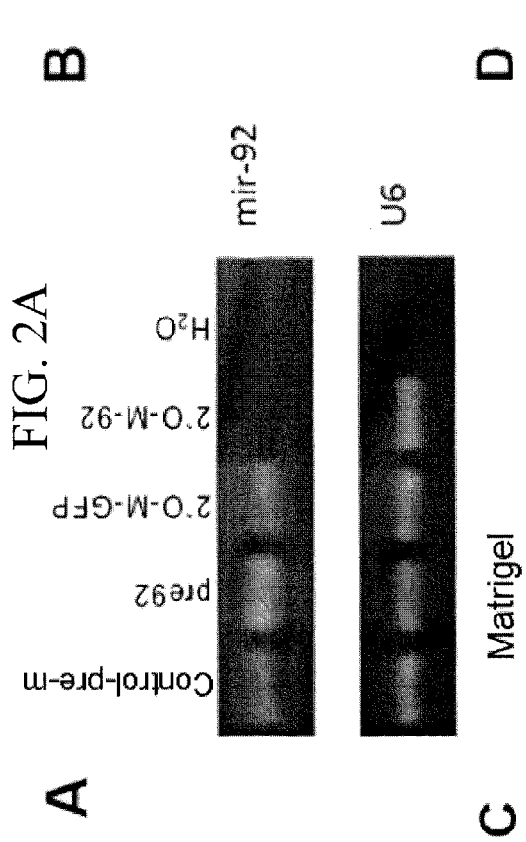
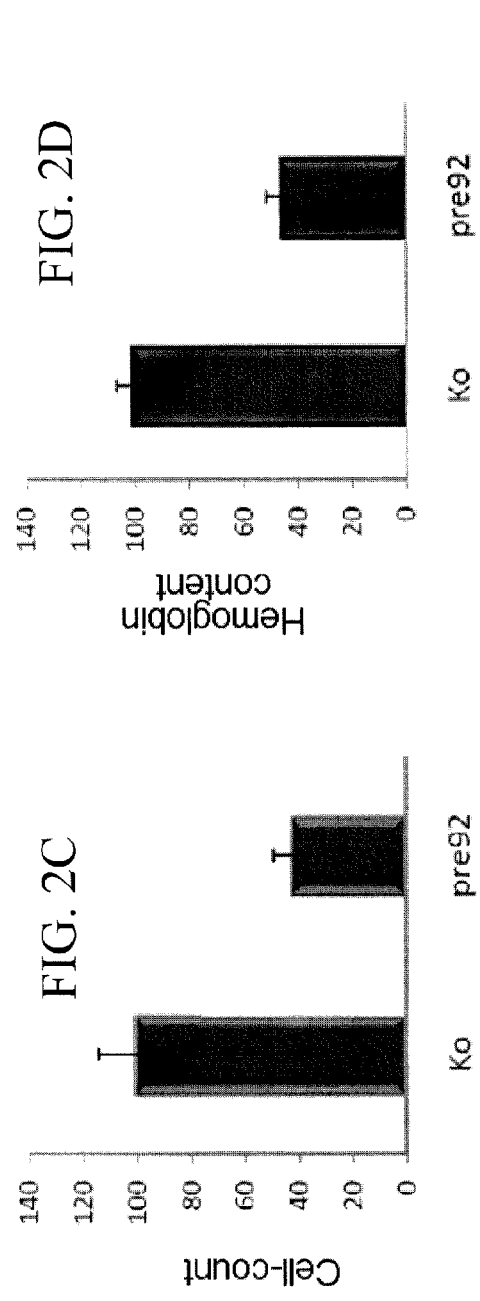
FIG. 2A
FIG. 2B
FIG. 2C
FIG. 2D

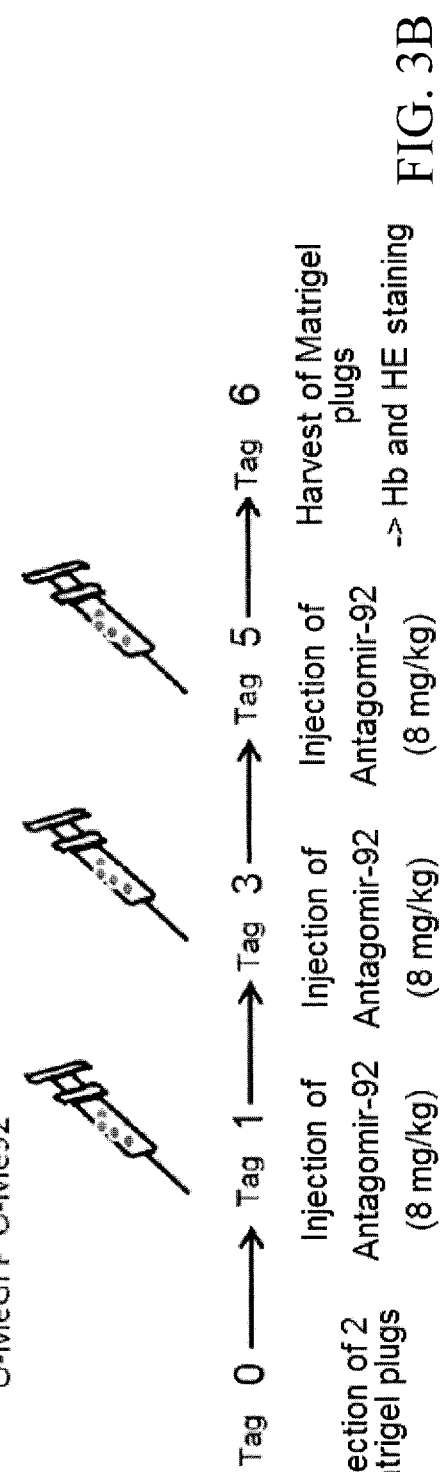
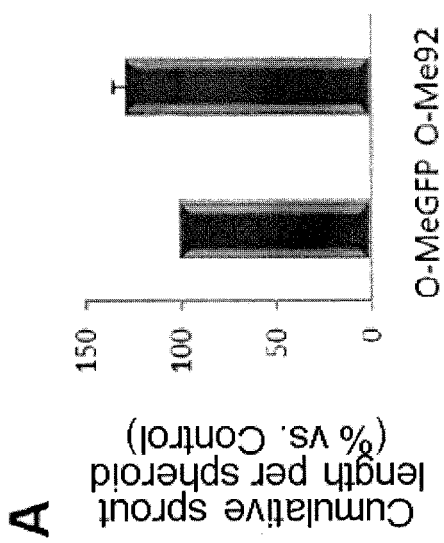
FIG. 3A
FIG. 3B

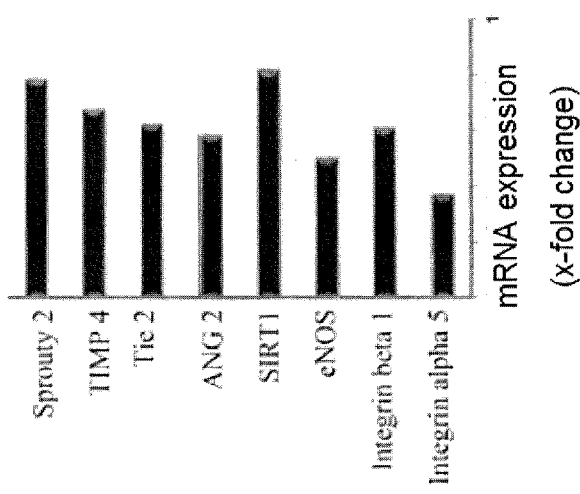
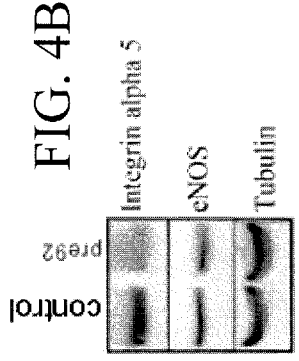
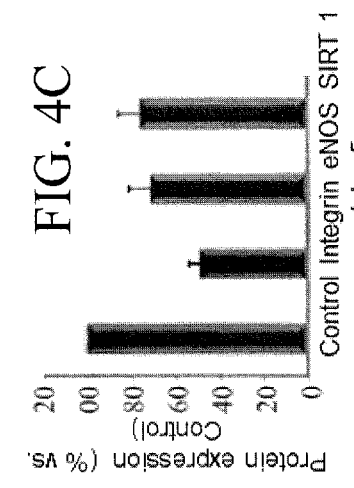
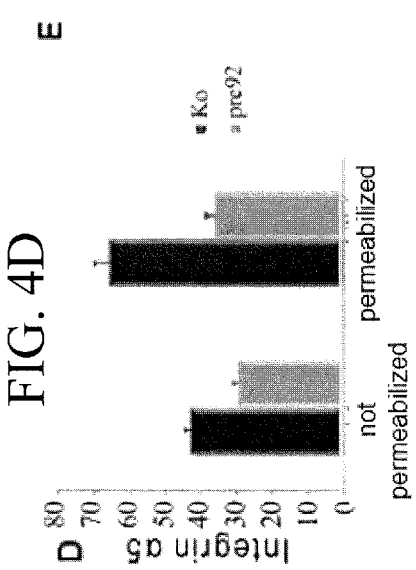
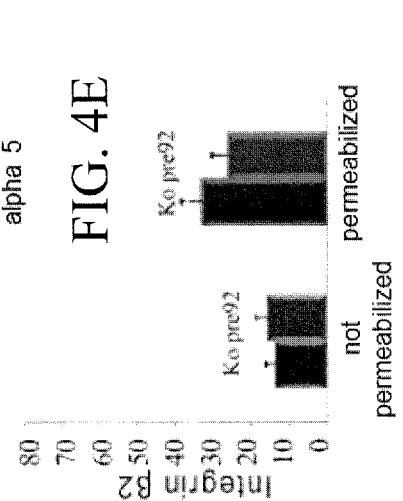
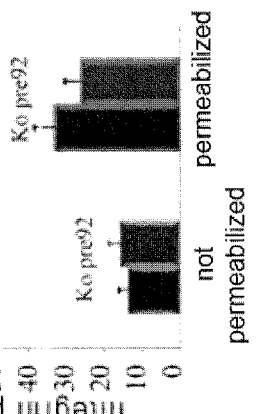
FIG. 4A, FIG. 4B, FIG. 4C, FIG. 4D, FIG. 4E

Impact of pre-miR-92 on angiogenesis in vitro
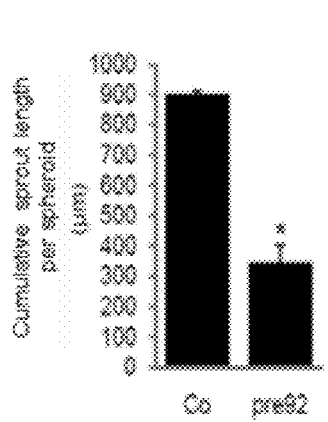 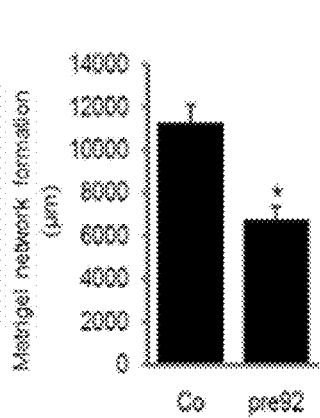 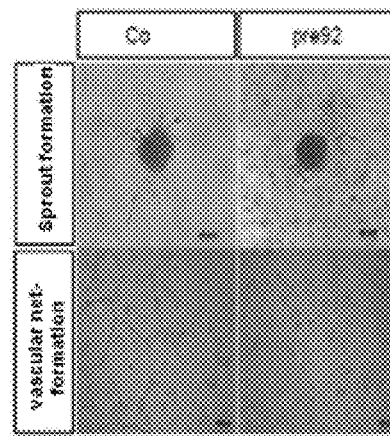
FIG. 5A          FIG. 5B          FIG. 5C
Impact of pre-miR-92 on angiogenesis in vivo
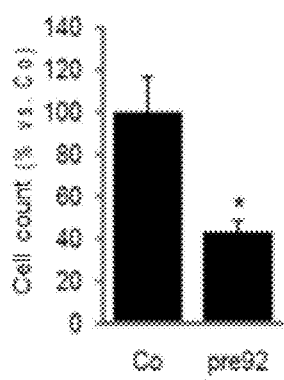 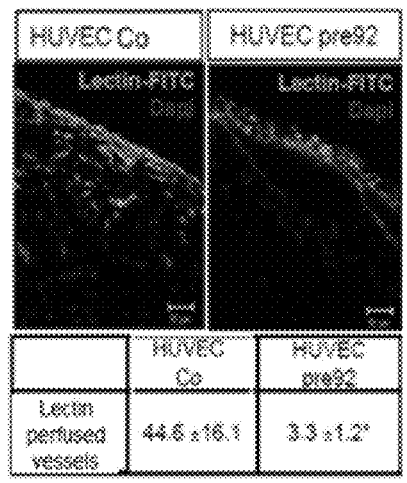 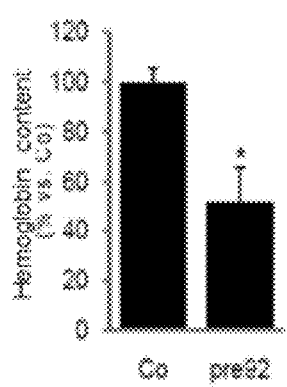
FIG. 5D          FIG. 5E          FIG. 5F Inhibition of miR-92a using antagomir-92a improves the formation of new vessels in the matrigel and hind limb ischemia model
Effect of antagomir-92a in the matrix model
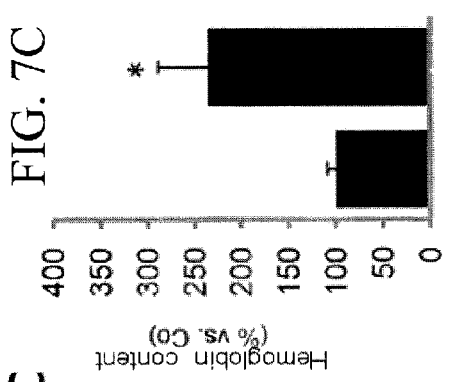
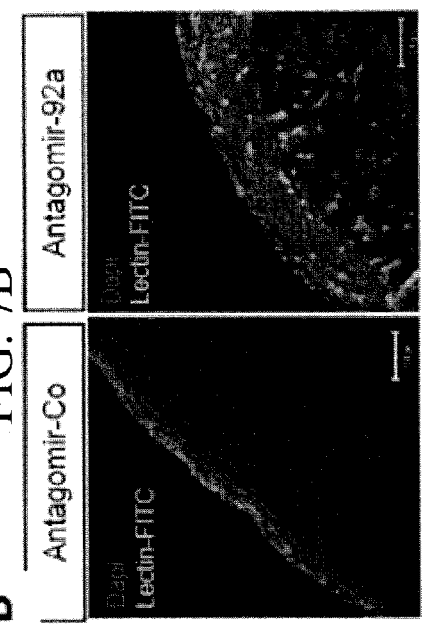
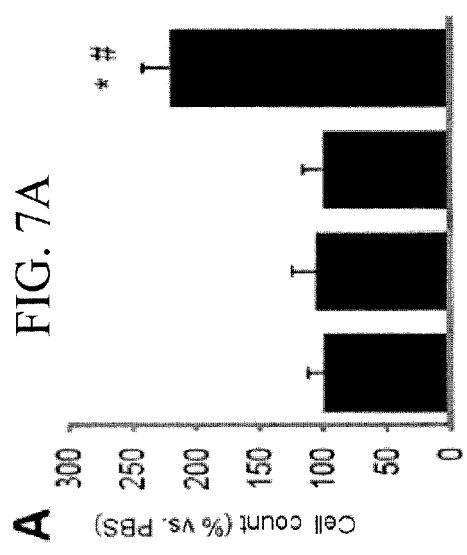

Effect of antagomir-92a in hind limb ischemia model
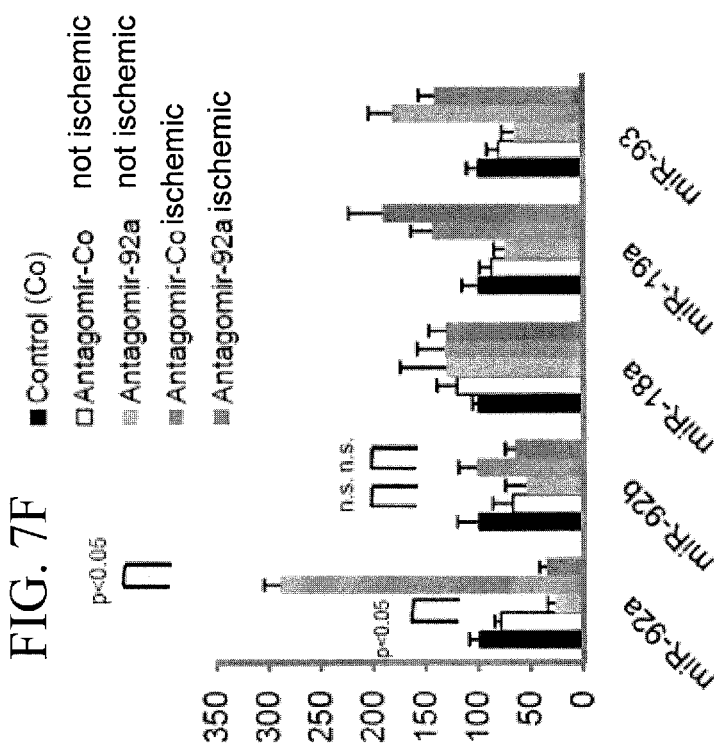
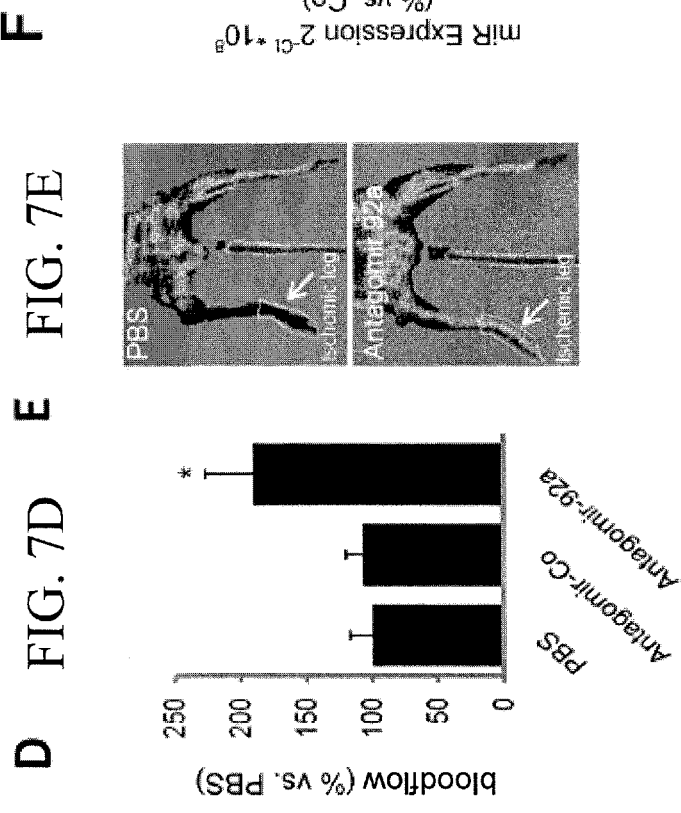

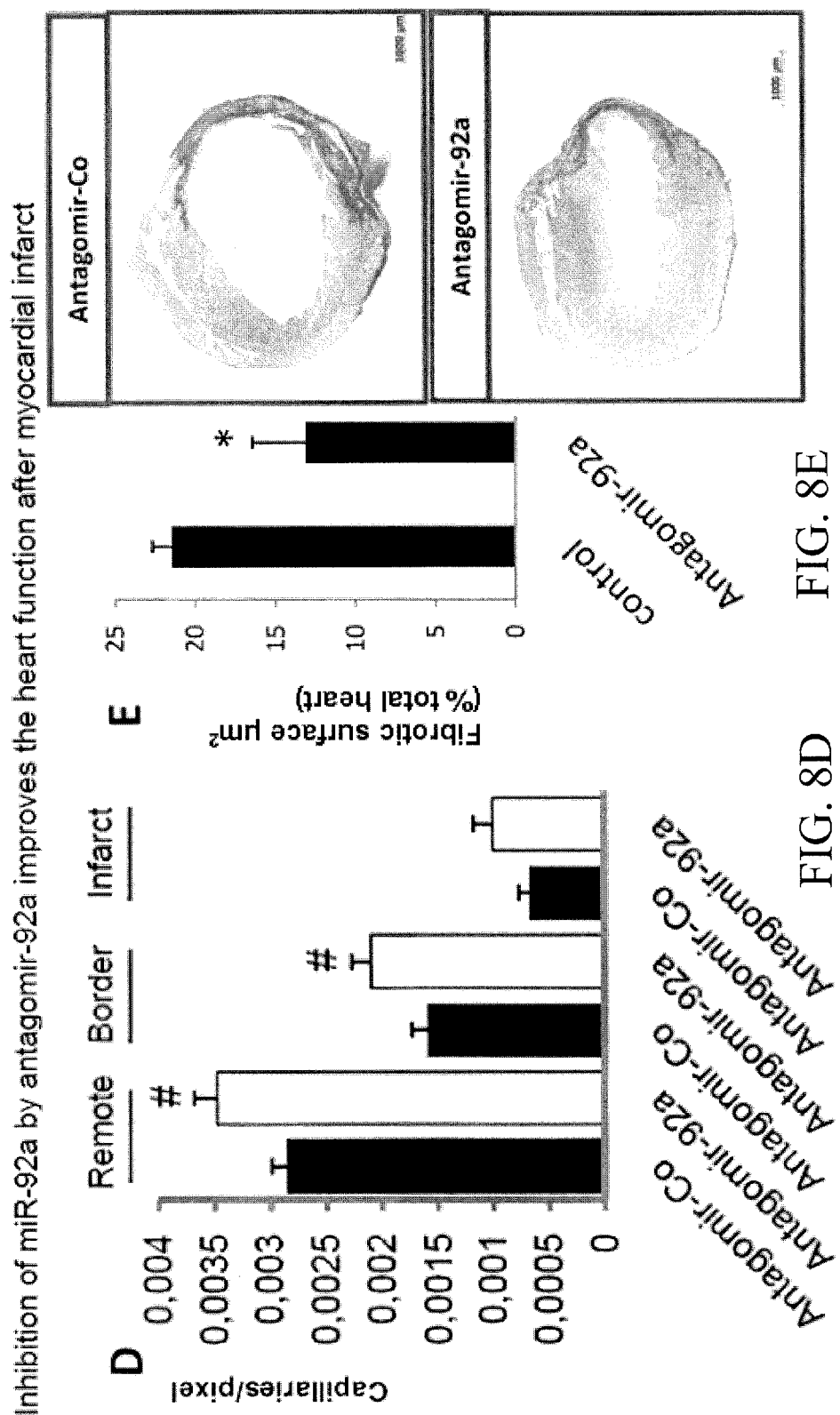

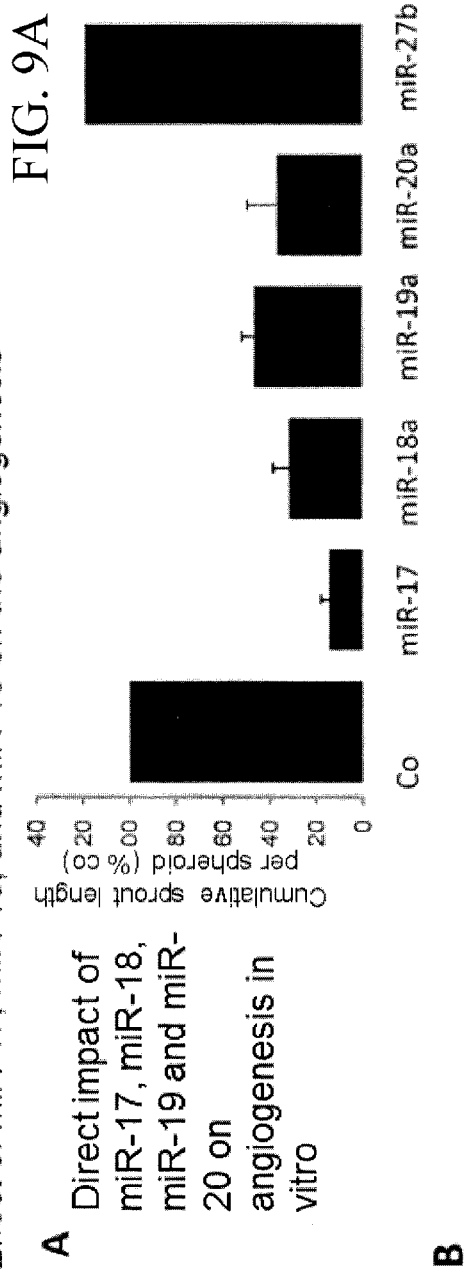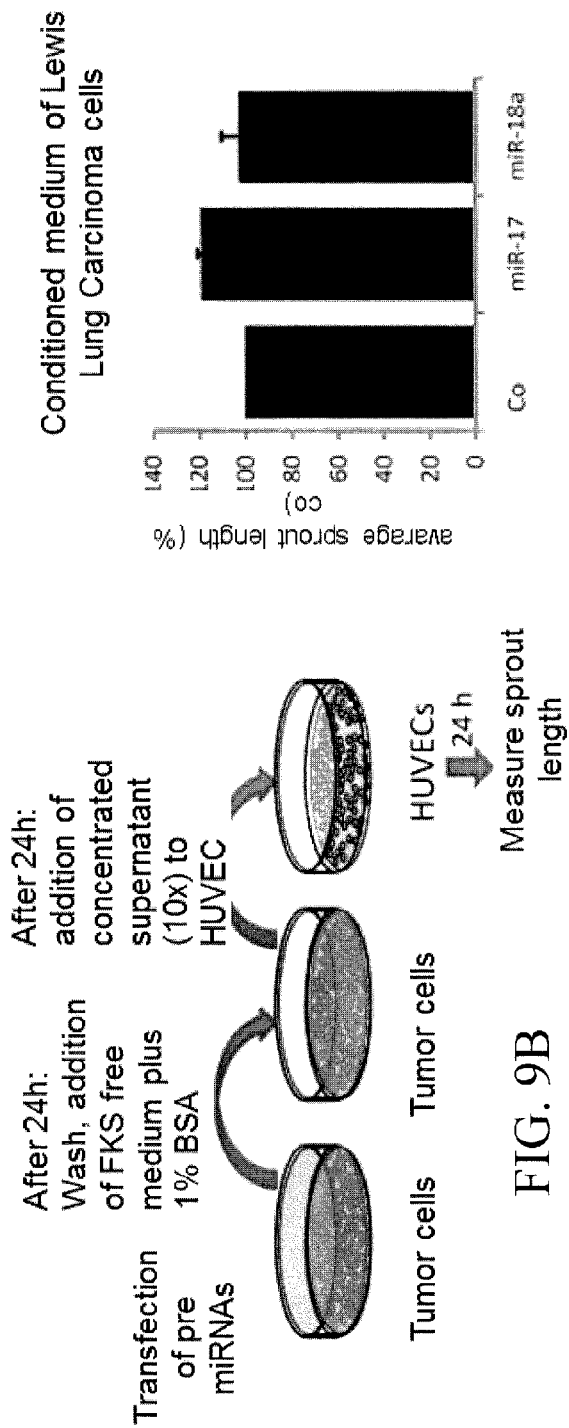
FIG. 9A
FIG. 9B

SEQUENCE LISTING

<160> NUMBER OF SEQ ID NOS: 11

<210> SEQ ID NO 1
<211> LENGTH: 78
<212> TYPE: RNA
<213> ORGANISM: Homo sapiens

<400> SEQUENCE: 1
cuuucuacac agguugggau cgguugcaau gcuguguuuc uguauggguau ugcacuuguc    60 ccggccuguu gaguuugg                                                  78

<210> SEQ ID NO 2

-continued

```
<211> LENGTH: 75
<212> TYPE: RNA
<213> ORGANISM: Homo sapiens

<400> SEQUENCE: 2
ucaucccugg gugggauuuu guugcauuac uuguguucua auaaaguau ugcacuuguc    60 ccggccugug gaaga                                                    75

<210> SEQ ID NO 3
<211> LENGTH: 96
<212> TYPE: RNA
<213> ORGANISM: Homo sapiens

<400> SEQUENCE: 3
cgggccccgg gcgggcggga gggacgggac gcggugcagu guuguuuuuu cccccgccaa    60
uauugcacuc gucccggccu ccggccccccc cggccc                             96

<210> SEQ ID NO 4
<211> LENGTH: 22
<212> TYPE: RNA
<213> ORGANISM: Homo sapiens

<400> SEQUENCE: 4
uauugcacuu gucccggccu gu                                             22

<210> SEQ ID NO 5
<211> LENGTH: 22
<212> TYPE: RNA
<213> ORGANISM: Homo sapiens

<400> SEQUENCE: 5
uauugcacuc gucccggccu cc                                             22

<210> SEQ ID NO 6
<211> LENGTH: 21
<212> TYPE: RNA
<213> ORGANISM: artificial
<220> FEATURE:
<223> OTHER INFORMATION: antisense oligoribonucleotide against miR-92

<400> SEQUENCE: 6
caggccggga caagugcaau a                                              21

<210> SEQ ID NO 7
<211> LENGTH: 22
<212> TYPE: RNA
<213> ORGANISM: artificial
<220> FEATURE:
<223> OTHER INFORMATION: 2'O-methyl-antisense oligoribonucleotide
      against GFP
<220> FEATURE:
<221> NAME/KEY: misc_feature
<222> LOCATION: (1)..(22)
<223> OTHER INFORMATION: 2'O-methyl modified nucleotide

<400> SEQUENCE: 7
aaggcaagcu gacccugaag uu                                             22

<210> SEQ ID NO 8
<211> LENGTH: 22
<212> TYPE: RNA
<213> ORGANISM: Artificial
<220> FEATURE:
<223> OTHER INFORMATION: antisense oligoribonucleotide against miR-92
```

```
<400> SEQUENCE: 8
acaggccggg acaagugcaa ua                                                22

<210> SEQ ID NO 9
<211> LENGTH: 21
<212> TYPE: RNA
<213> ORGANISM: artificial
<220> FEATURE:
<223> OTHER INFORMATION: 2'O-methyl modified antisense
      oligoribonucleotide against miR-92
<220> FEATURE:
<221> NAME/KEY: misc_feature
<222> LOCATION: (1)..(2)
<223> OTHER INFORMATION: phosphothioate bond
<220> FEATURE:
<221> NAME/KEY: misc_feature
<222> LOCATION: (2)..(3)
<223> OTHER INFORMATION: phosphothioate bond
<220> FEATURE:
<221> NAME/KEY: misc_feature
<222> LOCATION: (18)..(19)
<223> OTHER INFORMATION: phosphothioate bond
<220> FEATURE:
<221> NAME/KEY: misc_feature
<222> LOCATION: (19)..(20)
<223> OTHER INFORMATION: phosphothioate bond
<220> FEATURE:
<221> NAME/KEY: misc_feature
<222> LOCATION: (20)..(21)
<223> OTHER INFORMATION: phosphothioate bond
<220> FEATURE:
<221> NAME/KEY: misc_feature
<222> LOCATION: (21)..(21)
<223> OTHER INFORMATION: 3' cholesterol group
<220> FEATURE:
<221> NAME/KEY: misc_feature
<222> LOCATION: (21)..(21)
<223> OTHER INFORMATION: phosphothioate

<400> SEQUENCE: 9
caggccggga caagugcaau a                                                 21

<210> SEQ ID NO 10
<211> LENGTH: 22
<212> TYPE: RNA
<213> ORGANISM: artificial
<220> FEATURE:
<223> OTHER INFORMATION: 2'O-methyl-modified antisense
      oligoribonucleotide against miR-92
<220> FEATURE:
<221> NAME/KEY: misc_feature
<222> LOCATION: (1)..(2)
<223> OTHER INFORMATION: phosphothioate bond
<220> FEATURE:
<221> NAME/KEY: misc_feature
<222> LOCATION: (2)..(3)
<223> OTHER INFORMATION: phosphothioate bond
<220> FEATURE:
<221> NAME/KEY: misc_feature
<222> LOCATION: (3)..(4)
<223> OTHER INFORMATION: phosphothioate bond
<220> FEATURE:
<221> NAME/KEY: misc_feature
<222> LOCATION: (19)..(20)
<223> OTHER INFORMATION: phosphothioate bond
<220> FEATURE:
<221> NAME/KEY: misc_feature
<222> LOCATION: (20)..(21)
<223> OTHER INFORMATION: phosphothioate bond
<220> FEATURE:
<221> NAME/KEY: misc_feature
<222> LOCATION: (21)..(22)
<223> OTHER INFORMATION: phosphothioate bond
<220> FEATURE:
<221> NAME/KEY: misc_feature
```

```
<222> LOCATION: (22)..(22)
<223> OTHER INFORMATION: 3' cholesterol group
<220> FEATURE:
<221> NAME/KEY: misc_feature
<222> LOCATION: (22)..(22)
<223> OTHER INFORMATION: phosphothioate

<400> SEQUENCE: 10
acaggccggg acaagugcaa ua                                              22

<210> SEQ ID NO 11
<211> LENGTH: 21
<212> TYPE: RNA
<213> ORGANISM: artificial
<220> FEATURE:
<223> OTHER INFORMATION: 2'O-methyl-modified antisense
      oligoribonucleotide against miR-92
<220> FEATURE:
<221> NAME/KEY: misc_feature
<222> LOCATION: (1)..(21)
<223> OTHER INFORMATION: 2'O-methyl-modified nucleotide

<400> SEQUENCE: 11
caggccggga caagugcaau a                                               21
```

METHOD FOR THE INHIBITION OF ANGIOGENESIS

CROSS-REFERENCE TO A RELATED APPLICATION

This application is a Divisional Application of U.S. application Ser. No. 14/448,119, filed Jul. 31, 2014 (now U.S. Pat. No. 9,279,123); which is a Continuation Application of U.S. application Ser. No. 13/569,786, filed Aug. 8, 2012 (now U.S. Pat. No. 8,912,158); which is a Continuation Application of U.S. application Ser. No. 12/739,876, filed Jul. 22, 2010 (now U.S. Pat. No. 8,258,113); which is a National Stage Application of International Application No. PCT/DE2008/001759, filed Oct. 30, 2008; which claims priority to German Application No. 10 2007 052 114.8, filed Oct. 30, 2007; all of which are incorporated herein by reference in their entirety.

The Sequence Listing for this application is labeled "SeqList-30Jul14-ST25.txt", which was created on Jul. 30, 2014, and is 5 KB. The entire contents is incorporated herein by reference in its entirety.

FIELD OF THE INVENTION

The invention relates to a method for influencing the miR-92 expression in a cell, in particular for promoting the angiogenesis, vascularization or vessel repair, or for inhibiting or blocking tumor angiogenesis, and the use of such a method for the therapy of a disease or a condition. Furthermore, the invention relates to a pharmaceutical composition for promoting angiogenesis, vascularization or vessel repair, or for inhibiting or blocking tumor angiogenesis in a cell.

BACKGROUND OF THE INVENTION

The endothelium plays an important role in the maintenance of the integrity and functionality of the vessels. In the adult, the growth of new vessels occurs through arteriogenesis, angiogenesis or vasculogenesis. Whilst arteriogenesis is defined as the growth of collateral vessels, angiogenesis is understood as the growth of new blood vessels from pre-existing vessels. During angiogenesis, resting endothelial cells are activated by angiogenic factors and start to migrate, proliferate and organize themselves into tubular structures (2). The term vasculogenesis initially described the de novo blood vessel formation in the embryo from angioblasts, but now also includes the formation of blood vessels from endothelial precursor cells or other adult stem cells (1). Angiogenesis and vasculogenesis represent physiological developmental processes which play an essential role in the reconstitution of the blood flow in ischemic tissues, and are a basic step in the growth of tumors. The promotion of angiogenesis and neovascularization was identified as a possible therapeutic strategy in, for example, patients suffering from ischemia. In tumor angiogenesis, the limitation of these processes leads to a repression of tumor growth.

MicroRNAs (miRNAs) are small non-encoding RNAs that regulate the gene expression on the post-transcriptional level through a degradation of the target mRNA or through translational repression (3). In contrast to small interfering RNAs (siRNA), which bind to complementary mRNA sequences, the binding of the miRNA to a target does not only take place at a complementary RNA, but forms more complex RNA-RNA-structures that are thermodynamically preferred (4). This "incomplete" binding allows the binding of one miRNA molecule to different mRNA molecules. The regulation of a set of genes (in contrast to a monotherapy using a gene or a growth factor) can represent an advantage, if thereby complex regulatory processes can be influenced. So far, more than 400 miRNAs have been identified in the human genome, but the relevance of most of these miRNAs for the cellular function in physiological and pathologic processes is still unclear. Whereas it was described in the state of the art that the down-regulation of the miRNA-processing enzymes Dicer and Drosha impedes angiogenesis (5-7), only few specific miRNAs have been described which influence endothelial cell functions and angiogenesis. MiR-221 and miR-222 block the endothelial cell migration, proliferation and angiogenesis in vitro in an indirect manner through an interaction with the stem cell factor receptor c-kit and regulation of the eNOS expression (6, 8). In contrast to this, the expression of let7-f and miR-27b contributes to an in vitro angiogenesis (7).

The state of the art attributed a strong tumor angiogenesis-promoting activity to the miRNA cluster miR-17-92. The miR-17-92 cluster consists of miR-17-5p, miR-17-3p, miR-18a, miR-19a, miR-20a, miR-19b, and miR-92-1 (9). This miR-17-92 cluster is up-regulated in Myc-induced tumors, and the individual miRNAs miR-18 and miR-19 could be identified as molecules which specifically interact with the expression of anti-angiogenic proteins. A specific evaluation of the targets of these miRNAs showed that miR-18 preferably suppresses the expression of the connective tissue growth factor (CTGF), whereas miR-19 interacts with the strong angiogenesis-inhibitor thrombospondin-1 (TSP-1) (10).

BRIEF SUMMARY

It was surprisingly found in accordance with the invention that miR-92 does not promote the angiogenesis as described in the state of the art, but strongly reduces the migration and tube formation of endothelial cells in vitro and the neovascularization in vivo. The inhibition of miR-92 increases neovascularization. Accordingly, miR-92 has an anti-angiogenic activity and not a pro-angiogenic activity as described so far in the state of the art.

This anti-angiogenic activity is connected to the inhibition of key proteins that control angiogenesis and endothelial activity, including the endothelial nitric oxide synthase (eNOS), and sirtuin1 (SIRT1), which are both essential for postnatal endothelial cell functions (11 to 13), and integrin a5, which controls the endothelial cell motility and the interaction with the matrix (14). The inhibition of miR-92 by miR-92 inhibitors represents a new therapeutic strategy for improving the endothelial cell function and neovascularization. At the same time, it was found that the over-expression of miR-92 reduces neovascularization.

DESCRIPTION OF THE INVENTION

The invention is based on the finding that miR-92 exerts an anti-angiogenic biological activity, and not a pro-angiogenic activity as described in the state of the art so far.

More specifically, the invention relates to a method for influencing the miR-92 expression in a cell, in particular in the context of angiogenesis and/or vasculogenesis. According to the invention, the method comprises the following steps:

a) Providing a cell; and
b1) Reducing the miR-92 expression in the cell in order to promote angiogenesis, vascularization and/or the vessel repair by introducing an antisense molecule against miR-92 into the cell, or b2) Increasing the miR-92 expression in the cell for an inhibition of the tumor angiogenesis by introducing a construct into the cell, wherein said construct includes an expressible miR-92 sequence. It is also possible, to introduce miR-92 into the cell.

In a preferred embodiment, said method is an in vitro method.

The term reducing or increasing of the miR-92 expression in the cell is based on a comparison with the miR-92 expression in a wild-type cell, as can be performed using RT-PCR or real-time PCR. The respective change of the expression can also be determined using the functional effects of the modified expression level of miR-92 on the characteristics of the cell.

An antisense molecule is a single-stranded molecule having a sequence which is essentially reverse complementary to an RNA (here miR-92), and which inhibits the biological function of miR-92 through hybridization with the miR-92. Preferably, the molecule is an antisense RNA, which optionally can comprise chemical modifications.

The construct can be a plasmid, a cosmid, a virus or a precursor-miRNA, wherein the construct advantageously includes a means for the transcription of the expressible miR-92 sequence as included, such as, for example, a promoter which is functionally linked with the miR-92 sequence.

The term "miR-92" as used herein includes both precursor molecules, such as pre-92a-1, pre-92a-2, and pre-92b, as well as processed molecules, such as miR-92a, and miR-92b (see also the sequences according to SEQ ID NO 1 to 5).

The introduction of a molecule or a construct can take place using both physical methods (such as microinjection or electroporation), by means of chemical methods (such as with calcium phosphate or lipofection), or by means of viral methods (using viruses).

In a preferred embodiment of the invention, influencing of the expression of a protein in the cell results from influencing the miR-92 expression in a cell, wherein said protein is selected from the group of: eNOS, SIRT1, integrin alpha 5, integrin beta 1, integrin alpha v, Sprouty 2, TIMP 4, Tie 2, ANG 2, MKK 4, KLF 2, PCAF, EDG 1 and RAP 1B. All these proteins are associated with the control of the endothelial cell function, the athero-protection, and/or the postnatal neovascularization. SIRT1 is furthermore associated with age-related diseases.

Providing a cell comprises both the provision of a cell in isolated form, such as, for example, a cell of a clonal cell line, as well as the provision of a cell as part of a tissue, an organ or an organism.

The cell as provided can generally comprise any kind of cell. Preferably, the cell as provided is a vascular cell, a hematopoietic cell, a heart muscle cell, an inflammatory cell, and/or a neuronal cell. This in each case includes all precursor cells and stem cells of the cells as indicated. In a preferred embodiment of the method, the stem cell is not a human embryonic stem cell. Furthermore, the cell as provided can be present isolated, but also in association with a tissue or an organ. In one embodiment, the method can also be performed in vivo.

The cell as provided preferably stems from a metazoan, in particular from a mammal (such as, for example, a rodent, such as mouse or rat), a monkey, a great ape, a bovine, a pig, a dog or a cat or, particularly preferred, from a human.

Reduction of the miR-92 Expression

In as much as the method leads to a reduction of the miR-92 expression in the cell compared to the normal expression of miR-92 in a wild-type cell, the reduction of the expression takes place through providing a molecule selected from the group consisting of antisense molecules, synthetic miR-92 inhibitors, and transcription factor inhibitors. This reduction of the miR-92 expression leads to, for example, an increase of the vascularization and vessel repair in the tissue.

In one embodiment of the method according to the invention, the antisense molecule is a molecule which hybridizes with an RNA-molecule according to one of SEQ ID NO: 1 to 5, both under stringent as well as under less stringent conditions. This includes the possibility that in the hybridized state the antisense molecule exhibits "mismatches" when compared with miR-92, which, nevertheless, do not eliminate the function as an antisense molecule. Therefore, despite the base mismatch(es), an inhibition or degradation of miR-92 takes place. In particular, the antisense molecule can have a length of up to 80 nucleotides, preferably up to 30 nucleotides, particularly preferred of 15 to 22 nucleotides. Particularly for an inhibition of the immature miR-92 precursor, the antisense molecule can have up to 80 nucleotides, in particular up to 30 nucleotides. The minimal length of such an antisense molecule is advantageously 12 nucleotides, preferably 15 nucleotides.

In a preferred embodiment, the antisense molecule includes a sequence that is reverse complementary to a sequence according to one of SEQ ID NO 1 to 5. Thereby, no base mismatch(es) are formed, which leads to an efficient inhibition of the miR-92. In a preferred embodiment of the invention, the antisense molecule is a molecule with a sequence according to SEQ ID NO 6 or 8. It is possible that the antisense molecule includes at least one chemical modification, such as, for example, at least one 2'-O-methyl-, cholesterol-, phosphothioate-, and/or 2'-O-methoxyethyl-2'-fluoro-group. The antisense molecule can also or additionally include locked nucleic acid (LNA) components. For example, a very much preferred embodiment of the antisense molecule is the following molecule, which includes a sequence according to SEQ ID NO 6 with chemical modifications:

(SEQ ID NO 9)
C$_t$A$_t$GGCCGGGACAAGUGCA$_t$A$_t$U$_t$A$_t$-Chol wherein the capital letters indicate 2'-O-methyl modified nucleotides, the subscripted t ("$_t$") indicates a phosphothioate bond between adjacent nucleotides, and "Chol" indicates a cholesterol group.

A very much preferred embodiment of the antisense molecule including a sequence according to SEQ ID NO 8 with chemical modifications is the following molecule:

(SEQ ID NO 10)
A$_t$C$_t$A$_t$GGCCGGGACAAGUGCA$_t$A$_t$U$_t$A$_t$-Chol wherein the capital letters indicate 2'-O-methyl modified nucleotides, the subscripted t ("$_t$") indicates a phosphothioate bond between adjacent nucleotides, and "Chol" indicates a cholesterol group.

Furthermore preferred is an antisense molecule including a sequence according to SEQ ID NO 11 including only 2'-O-methyl modified nucleotides.

Methods for a Synthesis of Such Antisense Molecules are Known to the Person of Skill.

A method of the kind as described above for promoting the angiogenesis, vascularization and vessel repair can be used for a therapy of a disease or a condition. The disease or the (optionally pathological) condition is selected from the group consisting of ischemia (such as, for example, myocardial infarct, chronic ischemic heart disease, peripheral or coronary artery occlusion, ischemic infarct, stroke), pathological angiogenesis (such as, for example, tumor angiogenesis, metastases formation, diabetic retinopathy, chronic inflammatory diseases), arthrosclerosis, secondary diseases to arthrosclerosis (acute coronary syndrome, myocardial infarct, stroke, cardiomyopathy) or (premature) aging or aging-associated diseases, as well as neurodegenerative diseases, such as Morbus Alzheimer, and Morbus Parkinson.

Furthermore, the method as described can be used for the treatment of stem cells or precursor cells (such as, for example, pro-angiogenic cells, organ-specific precursor cells, bone-marrow derived cells or circulating precursor cells).

Thus, the method can be used both in vivo, and ex vivo or in vitro, such as, for example, for the production of vessel replacement material, in particular for tissue replacement therapy, or in research.

Increasing the miR-92 Expression

In as much as in the method the expression of miR-92 in a cell, e.g. in an endothelial cell, is increased compared with the normal expression of miR-92 in a wild-type cell, this, for example, can take place through an increase of the expression by means of introducing of a construct including an expressible miR-92 sequence into the cell. In a preferred embodiment of the method according to the invention, the miR-92 construct includes an expressible sequence according to one of SEQ ID NO 1 to 5, or can express such a sequence, respectively. Advantageous embodiments of such a construct have been described above. Alternatively, miR-92 can also be introduced directly into the cell.

A method of the latter described kind for inhibiting the tumor angiogenesis can be used for a therapy of a disease or a (pathologic) condition selected from the group consisting of overshooting angiogenesis, undesired angiogenesis, tumors and chronic inflammations.

Pharmaceutical Composition

The invention furthermore relates to a pharmaceutical composition, comprising either an agent for reducing the miR-92 activity or expression in a cell in the form of an antisense molecule against miR-92, an, optionally synthetic, inhibitor and/or a transcription factor inhibitor; or an agent for increasing the miR-92 expression in a cell in the form of a construct for expressing miR-92. Thereby, the construct can comprise or include an expressible sequence according to one of SEQ ID NO 1 to 5. In one embodiment, the antisense molecule against miR-92 included in the pharmaceutical composition includes a sequence according to SEQ ID NO 6, 8 or 11. For additional preferred embodiments of the constructs or of the antisense molecule, reference is made to the description as above and included herein.

The invention furthermore relates to a method for producing the above-described pharmaceutical compositions.

The pharmaceutical composition according to the invention can be present in the form of tablets, dragáes, pills, granulates, aerosoles, infusion solutions, emulsions, suspensions, solutions, or in or on the coating material of an implantable medical device, for example a stent, respectively.

The use according to the invention of the agent or the pharmaceutical composition, respectively, can take place using suitable known formulations.

The use according to the invention of the agents can be transformed in a known manner into the usual formulations, such as, for example, tablets, dragées, pills, granulates, aerosoles, emulsions, suspensions and solutions, using inert, non-toxic, pharmaceutically acceptable carriers or solvents. Hereby, the therapeutically effective agent concentration, with reference to the therapeutically effective compounds, shall be present each in a concentration of about 0.1 wt.-% to 95 wt.-%, preferably of about 0.5 wt.-% to 90 wt.-% of the overall mixture, i.e. in amounts that are sufficient in order to achieve the drug concentrations as required in the target tissue.

The formulations are, for example, produced by stretching of the agents with solvents and/or carriers, optionally using emulgators and/or dispersing agents, whereby, e.g., in case of the use of water as a diluent, optionally organic solvents can be used as auxiliary agents.

Further mentioned as auxiliary agents shall be e.g. water, non-toxic solvents, such as, for example, paraffin (e.g. crude oil fractions), plant oils (e.g. peanut oil, sesame oil), alcohols (e.g. ethyl alcohol, glycerol), carriers, such as, for example, natural stone dusts (e.g. kaolins, alumina, talcum, chalk), synthetic stone dusts (e.g. highly disperse silicic acid, silica), sugars (e.g. sucrose, lactose and glucose), emulgators (e.g. polyoxyethylene-fatty acid-esters, polyoxyethylene-fatty alcohol-ethers), dispersing agents (e.g. lignin, sulfite spent liquor, methyl cellulose, starch, and polyvinylpyrolidone), and lubricants (e.g. magnesium stearate, talcum, stearic acid, and sodium sulfate).

The administration takes place in a usual manner, preferably orally or parenterally, in particular perlingually or intravenously. In case of the oral use of the medicaments according to the invention, in addition to the carriers as indicated, tablets can of course also contain additives, such as, for example, sodium citrate, calcium carbonate and dicalcium phosphate together with different additives, such as starch, preferably potato starch, gelatin, and the like. Furthermore, lubricants, such as magnesium stearate, sodium lauryl sulfate and talcum, can also be used when producing tablets. In case of aqueous suspensions, in addition to the above-mentioned auxiliary agents, the drugs can be admixed with different taste-improving or coloring agents. For the case of a parenteral use, solutions of the drugs using suitable liquid carrier materials can be used.

Methods for Therapy or Prophylaxis

The invention also relates to a method for the therapy or prophylaxis of an individual, in particular a patient, using an miR-92 or an miR-92 antagonist (such as, for example, an antisense molecule or a transcription factor inhibitor) or a pharmaceutical composition in accordance with the description as above or contained herein. In the context of such a method, an amount of drug between 0.001 mg to 200 mg per kg body weight per day can be administered.

Antisense Molecule Against miR-92

The invention also relates to an antisense molecule against miR-92, comprising a sequence which hybridizes to a molecule of a sequence according to SEQ ID NO 1 to 5, wherein the molecule has or consists of up to 80 nucleotides, in particular 15 to 22 nucleotides. Such an antisense molecule advantageously comprises at least 12 nucleotides, preferably at least 15 nucleotides. The hybridization can take place under stringent or less stringent conditions. Methods for determining the hybridization are known to the person of skill.

Such a molecule can optionally include chemical modifications. Particularly preferred is a molecule according to SEQ ID NO: 6, 8 or 11, which includes at least one of the above-mentioned chemical modifications. Preferred antisense molecules including chemical modifications are the molecules according to SEQ ID NO: 9 and 10, which each are derived from the molecules according to SEQ ID NO: 6 or 8, respectively.

According to the invention, such a molecule can be used for promoting angiogenesis, vascularization and vessel repair.

According to the invention, miR-92 or a molecule with a sequence according to one of SEQ ID NO: 1 to 5 can be used for inhibiting tumor angiogenesis and in particular for producing a pharmaceutical composition as described above.

In particular, in a preferred embodiment thereof, the invention does not relate to processes for cloning human beings or processes for modifying the germ line genetic identity of human beings as well as uses of human embryos for industrial or commercial purposes or processes for modifying the genetic identity of animals which are likely to cause them suffering without any substantial medical benefit to man or animal, and also animals resulting from such processes.

The invention is explained in more detail based on examples, without being limited to these examples. The results of the experiments as described in the examples are depicted in the Figures.

DESCRIPTION OF THE FIGURES

The Figures show:

FIGS. 1A-1F: Effects of the over-expression of miR-92 on in vitro functions of endothelial cells (as provided cells).
- (A) Over-expression of miR-92 in pre-miR-92 transfected endothelial cells.
- (B/C) Inhibition of sprout formation in a spheroid (B) and a "matrigel assay" (C).
- (D/E/F) Effect of pre-miR-92 on the viability (D), migration (E), and adhesion (F).

FIGS. 2A-2D: Effect of the over-expression of miR-92 on angiogenesis in vivo.
- (A) Over-expression of miR-92 in pre-miR-92 transfected endothelial cells.
- (B/C/D) Inhibition of the angiogenesis in vivo. HUVEC were transfected with a control or with pre-miR-92, and $1 \times 10^6$ cells were implanted in in vivo "matrigel plugs". The angiogenesis was determined in H&E-sections (B/C), and the perfusion was determined by measuring of hemoglobin (D).

FIGS. 3A-3E: Effect of miR-92 inhibition on the in vitro and in vivo angiogenesis.
- (A) Stimulation of the in vitro sprouting using 2'O-methyl oligonucleotides blocking miR-92.
- (B/C/D/E) Effect of the systemic fusion of an antagomir on the in vivo neovascularization. (B) Experimental design, (C) Expression of miR-92 in different organs (heart, aorta, spleen, liver). (D) Effects on the perfusion according to the results of measuring the concentration of hemoglobin, (E) representative pictures (H&E-staining) for illustrating the formation of vessels.

FIGS. 4A-4E: Identification of miR-92 target molecules.
- (A) Gene expression profile HUVEC following treatment with pre-miR-92.
- (B/C) Confirmation of the dysregulation of the protein expression using Western Blot in HUVEC after transfection of pre-miR-92.
- (D/E) Detection of the effects of pre-miR-92 on the expression of integrin using FACS.

FIGS. 5A-5F: Effect of miR-92a on the angiogenesis in vitro (A-C) and in vivo (D-F).

In vitro: Pre-miR-92 was over-expressed in HUVEC, and the angiogenesis was determined in vitro in the spheroid model (A) and matrigel assay (B). N>3, *p<0.05 versus control (Co). Panel C shows representative examples.

In vivo: Pre-miR-92a or control microRNA (Co) transfected HUVEC were mixed with matrigel, and transplanted into nude mice. The vessel formation was determined using the cells as immigrated (D), determined in vivo in lectin-perfused vessels (E), and by determining the hemoglobin content (f). N>4, *p<0.05 versus control (Co).

Figure 6A:
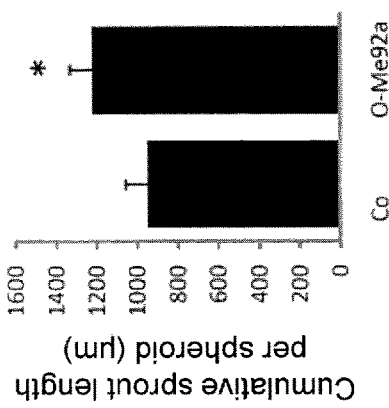
Figure 6B:
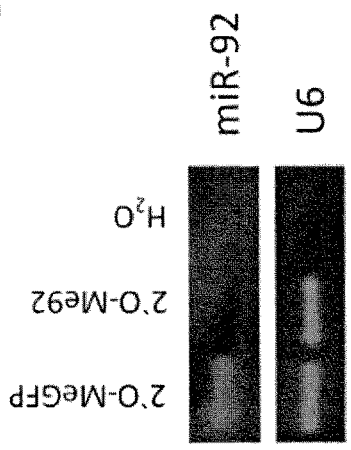
Figure 6C:
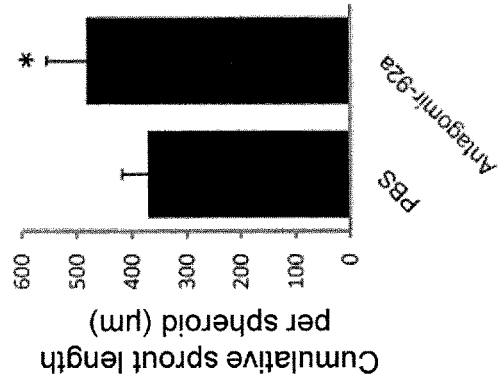
Figures 8A, 8B, 8C:
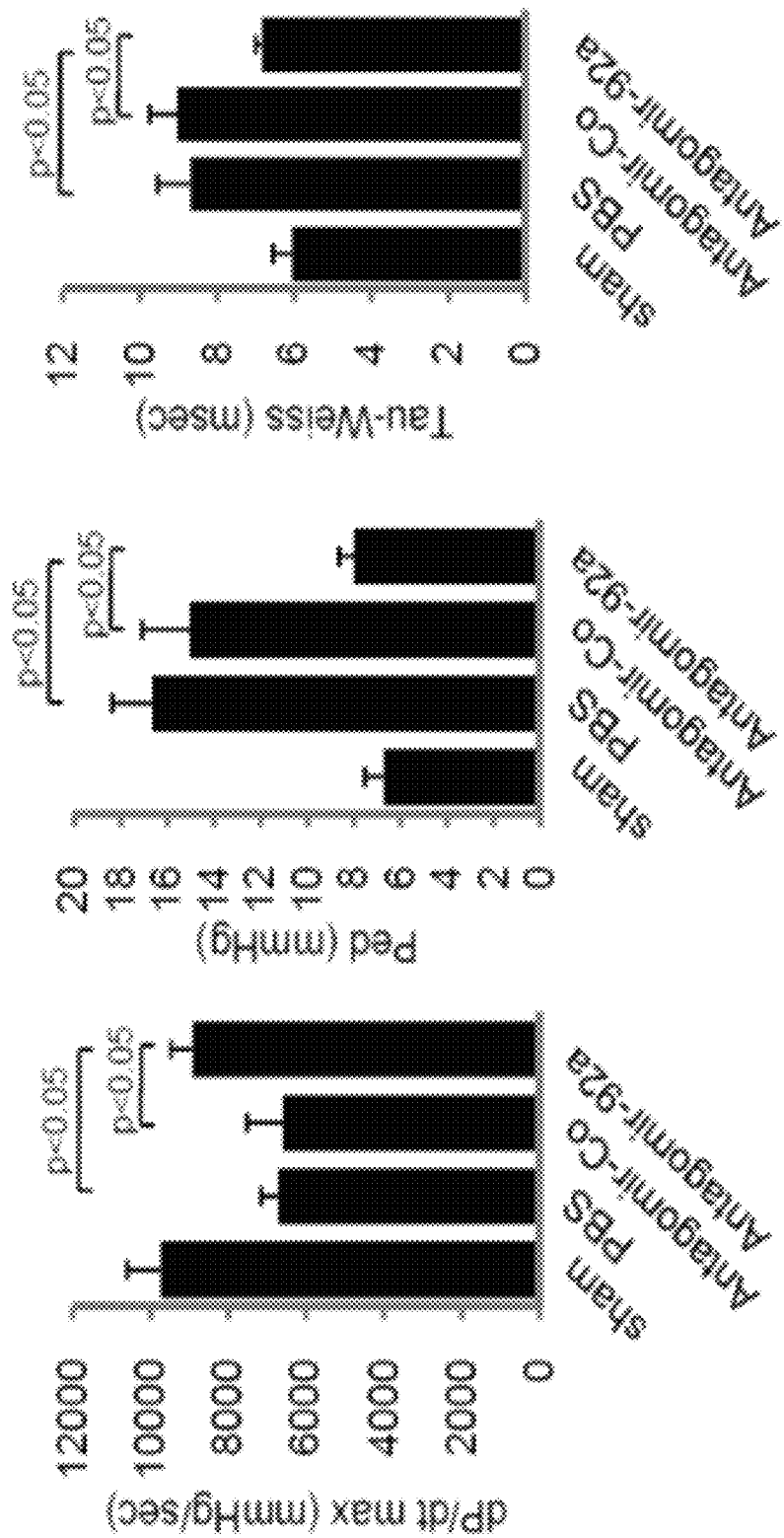

FIGS. 6A-6C: Effect of miR-92a inhibition on the angiogenesis in vitro.
- A/B) miR-92a was blocked by over-expression of 2'O-methyl antisense oligoribonucleotides, and the angiogenesis was determined in the spheroid model in vitro. N>3, *p<0.05 versus control oligonucleotides (Co) (2'OMeGFP).
- C) miR-92a was inhibited through the incubation with antagomir-92a, and the angiogenesis was determined in vitro in the spheroid model. N=5, *p<0.05 versus PBS control.

FIGS. 7A-7F: Effect of antagomir-92a on the formation of new vessels in the matrigel model (A-C), and hind limb ischemia model (D-F).

Antagomir-92a, 2 different control antagomirs or the solvent PBS were injected i.v. on day 1, 3, 5 (8 mg/kg bw), and the matrigel plugs were explanted on day 7. The numbers of immigrated cells (H&E, A), perfused lectin-positive vessels (B), and the hemoglobin content (C) were determined. N>4, p<0.05 versus PBS or antagomir-controls (Co). Antagomir-92a or controls were injected i.v. on day 0, 2, 4, 7, 9 after hind limb ischemia, and the perfusion was determined using laser Doppler (D, Example E). FIG. 7F shows the specificity of antagomir-92a on the expression of miR-92a and different other microRNAs. N>3, p<0.05 versus controls (Co).

FIGS. 8A-8E: Effect of antagomir-92a on the heart function after myocardial infarct. Antagomir-92a, control antagomir (antagomir-Co) or the solvent PBS were injected i.v. after induction of the cardiac infarct on day 0, 2, 4, 7, 9 (8 mg/kg bw), and the heart function was determined on day 14 using a Millar catheter. a-c show the determination of heart function parameters (a: contractility, b: pressure, c: relaxation constant). Antagomir-92a-treated animals all show better heart function parameters, when compared with the antagomir-Co and PBS group. 8D) shows the significant increase of the capillary in different regions of the heart after antagomir-92a treatment. 8E) shows the reduction of the size of infarct and fibrosis in the antagomir-92a treated group. All experiments N>5, *p<0.05 versus control (Co).

FIGS. 9A-9B: Effect of individual members of the miR-17-92 cluster on the angiogenesis in vitro.
- 9A) Direct effect of the over-expression of the individual microRNAs on the angiogenesis in the spheroid assay (N>3, *p<0.05).
- 9B) Paracrine effect of tumor cells which were transfected with miR-17 or miR-18 on the angiogenesis of endothelial cells. As depicted, tumor cells were transfected, and then the supernatant was added to endothelial cells (HUVEC) in order to test the effect of paracrine factors. The over-expression of miR-17 leads to an increase of the angiogenesis.

EXAMPLES

Materials and Methods

Cell Culture

Human umbilical vein endothelial cells (HUVEC) were purchased from Cambrex, and cultured until the third passage in endothelial basal medium (EBM; Cambrex) supplemented with hydrocortisone, bovine brain extract, epidermal growth factor and 10% fetal calf serum (FCS; Gibco). After the detachment with trypsin, the cells were cultured in 6 cm culture dishes for at least 24 to 48 hours.

Transfection

For the inhibition of miR-92, HUVECs were cultured up to a confluence of 60% to 70% before the transfection with the specific inhibitor. 2'-O-methyl-antisense oligoribonucleotides against miR-92 (5'-CAGGCCGGGACAAGUG-CAAUA-3', SEQ ID NO 11) or GFP (5'-AAGGCAAGCUGACCCUGAAGUU-3', SEQ ID NO 7) were synthesized by VBC Biotech, and 50 nmol/l were transfected with GeneTrans II® (MoBiTec) according to the protocol of the manufacturer. For over-expression of miR-92, HUVECs were cultured to a confluence of 50%. 10 nmol/l pre-miR-92 or control-pre-miR (Ambion) was transfected with lipofectamine RNAiMAX (Invitrogen) according to the protocol of the manufacturer.

Antagomir-Strategy

The single-stranded RNA as used herein consisted of 21 to 23 nucleotides and was synthesized by VBC Biotech as described (13). All animal models were held in a C57BL/6J background. Eight week old mice were subcutaneously injected along the abdominal middle line on day 0 with two matrigel basement matrix plugs, and received tail vain injections of a saline solution or an antagomir 92 on day 1, 3, and 5. Antagomir 92 was administered in dosages of 8 mg per kg body weight in 0.2 ml phosphate buffered saline (PBS) per injection. Tissue and matrigel plugs were harvested on day six. The tissue was frozen in liquid nitrogen, and stored at −80° C. for RNA analysis. For hemoglobin analysis, a matrigel plug was removed after seven days, and homogenized in 130 µl deionized water. After centrifugation, the supernatant was used in a Drabkin assay (Sigma-Aldrich) for measuring the hemoglobin concentration. Stock solutions of the hemoglobin were used for generating a standard curve. The results were expressed relative to the total protein in the supernatant. The second matrigel plug was used for the quantification of invading cells using H&E-staining.

Western Blot Analysis

For Western Blot analysis, HUVECs were lysed in RIPA lysis buffer (Sigma) for 20 minutes on ice. After centrifugation for 15 minutes at 20.000×g (4° C.) the protein content of the samples was determined according to the method of Bradford. Identical amounts of protein were loaded on a SDS-polyacrylamide gel, and blotted onto a PVDF- or nitrocellulose-membrane. Western blots were performed using antibodies against integrin a5 (rabbit polyclonal anti-integrin a5 antibody; 1:250, Chemicon), MKK4 (rabbit polyclonal anti-MKK4, 1:1.000, cell signaling), eNOS (mouse monoclonal anti-eNOS, 1:2.500, BD), SIRT1 (rabbit polyclonal anti-SIRT1, 1:1.000, Upstate) or tubulin (mouse monoclonal anti-tubulin; 1:1.500, Dianova).

RT-PCR

In order to determine the differential miRNA expression in HUVECs that were transfected with 2'-O-methyl antisense oligoribonucleotides against miR-92 or pre-miR-92, whole-RNA was isolated 24 hours after the transfection using TRIzol (Invitrogen) according to the protocol of the manufacturer. An RT-PCR was performed using the mirVana™ qRT-PCR miRNA detection kit (Ambion), and primer sets specific for the amplification of hsa-miR-92 (Ambion) (one cycle: 3 minutes at 95° C., 25 cycles: 15 seconds at 95° C., 30 seconds at 60° C.).

Migration Assay

In order to determine the migration of endothelial cells, HUVECs were detached with trypsin, harvested using centrifugation, and resuspended in 500 µl EBM with 0.1 BSA, counted and placed into the upper chamber of a modified Boyden chamber ($5\times10^4$ cells per chamber, pore size 8 µm, BD Biosciences), which was coated with 2.5 µg/l fibronectin. The chamber was placed into a culture dish with 24 wells containing EBM with 0.1% BSA and human vascular endothelial growth factor (VEGF, 50 ng/ml). Following an incubation for 5 hours at 37° C., the non-migrating cells on the upper side of the chamber were removed mechanically, and the remaining cells on the lower side were fixed with 4% formaldehyde. For quantification, the cell nuclei were stained with 4',6-diamidino-2-phenylindole (DAPI). Migrating cells on the lower side of the chamber were manually counted in five randomly chosen microscopic fields.

Vessel Formation Assay

HUVECs ($7\times10^4$) were cultured in a plate with 12 wells (Greiner) which were coated with 200 µl matrigel basement membrane matrix (BD Biosciences). The endothelial networks as formed were quantified after 24 hours in five randomly chosen microscopic fields using a computer-controlled microscope using the program KS300 3.0 (Zeiss).

Spheroid Based Angiogenesis Assay

Endothelial cell spheroids of a defined cell number were produced as described (22, 23). The in vitro angiogenesis was determined by measuring the cumulative length of the sprouted structures which were grown from each spheroid using a digital imaging software (Axioplan, Zeiss), whereby 10 spheroids were analyzed per experimental group and experiment.

MTT Viability Assay

For measuring the viability of the cells, the (3-(4,5-dimethylthiazol-2-yl)-2,5-diphenyl-2H-tetrazoliumbromide) (MTT assay) was used. 0.5 mg/ml MTT was added into each well 48 hours after transfection, and the cells were incubated for 4 hours at 37° C. The cells were washed with PBS, and lysed 30 minutes at room temperature with lysis buffer (40 nmol/l HCl in isopropanol). The absorption was photometrically measured at 550 nm.

Cell Matrix Adhesion

Cell culture plates with 96 wells were coated over night at 4° C. with 1 µg/ml soluble recombinant human collagen I (Roche, Mannheim, Germany) or 2.5 µg/ml human fibronectin (Roche, Mannheim, Germany) in PBS, and then incubated for one hour at room temperature with 3% (w/v) heat-inactivated (2 hours, 56° C.) human serum albumin (HSA). HUVECs were stained with 2',7'-bis-(2-carboxyethyl)-5-(and-6)-carboxy fluorescein acetoxy methylester (BCECF-AM) or CellTracker Green (Molecular Probes, Eugene, Oreg.), and were resuspended in EBM with 0.05% HSA after the detachment with trypsin. Then, 50.000 cells per well were seeded in the coated wells in 100 µl EBM with 0.05% HSA, and incubated for 60 minutes at 37° C. After washing out of the non-adherent cells using warm EBM, the adherent cells were quantified three times with a fluorescence plate reader (Fluostat, BMG Lab Technologies, Offenburg, Germany).

Flow Cytometry Analysis

For a permeabilization, HUVECs that were transfected with pre-miR-92 or control were detached with trypsin, fixed in 4% formaldehyde for 10 minutes, and treated with 0.1% tritonX-100. The cells (permeabilized and non-permeabilized) were blocked using 1% BSA, and stained with integrin a5 (anti-CD49e-FITC 1:10, Immunotech) or integrin b1 (anti-CD29-APC 1:20, BD) antibodies. The cells were analysed with a FACS Canto II device (BD).

In Vivo Matrigel Plug Assay

This assay was performed as described (24), but with the following modifications: HUVECs were transfected with pre-miR-92, or for a control as described above. 18 hours after the transfection the cells were labeled with "cell tracker CM-DiI" (Invitrogen), detached, washed and counted. $1 \times 10^6$ cells were resuspended in 30 µl PBS and mixed with 500 µl "matrigel basement membrane matrix" (BD Biosciences) containing 15 units heparin (Sigma-Aldrich). The cell-matrigel-mix was injected subcutaneously into six to eight week old female athymic nude mice (Harlan), along the abdominal middle line. Hemoglobin analysis and H&E-staining were performed as described above.

Affymetrix mRNA Profiling

HUVECs were transfected with pre-miR-92, or for a control. Whole RNA was isolated after 48 hours, and the gene expression profile was measured using an Affymetrix-gene-chip-expression assay.

Results

Pre-miR-92 Blocks Endothelial Cell Functions In Vitro and In Vivo

In order to test the effect of miR-92 on endothelial cells, HUVECs were transfected with the miR-92 precursor pre-miR-92, and the effect of this transfection was determined in different in vitro assays. The efficient over-expression of miR-92 was first detected using RT-PCR (FIG. 1A). The miR-92 over-expression significantly blocked the formation of vessel structures in a spheroid assay (FIG. 1B), and inhibited the formation of a vascular network in matrigels (FIG. 1C), which indicates that miR-92 is a negative regulator of the angiogenesis in vitro. In order to detect a possible toxic effect of miR-92, the cell viability was measured. Thereby after transfection of pre-miR-92 no significant differences could be detected, compared with non-transfected cells (FIG. 1D). Since the endothelial cell migration is of large importance for the angiogenic activity of cells in vitro, in addition the migration of HUVEC under basal conditions and as a response to VEGF was determined. Pre-miR-92 reduced the migration (FIG. 1E) and the adhesion of the cells to fibronectin (FIG. 1F). Thus, pre-mir-92 shows no direct toxic effect, but blocks the endothelial cell response, which is required for the angiogenesis. Furthermore, the effect of pre-miR-92 on the angiogenesis in vivo was determined. For this, HUVECs transfected with pre-miR-92 were implanted in a matrigel plug into nude mice in vivo. The efficiency of the inhibition was each controlled in a sub-fraction of the implanted cells (FIG. 2A). As shown in the representative pictures of FIG. 2B and the quantification in FIG. 2C, pre-miR-92 blocks the growth of the vessels in vivo in an efficient manner. In addition, the perfusion is significantly reduced, as could be shown by measuring the hemoglobin concentration in the explanted matrigel plugs (FIG. 2B).

Inhibition of miR-92 Increases the Angiogenesis In Vitro and In Vivo

Figure 3C:
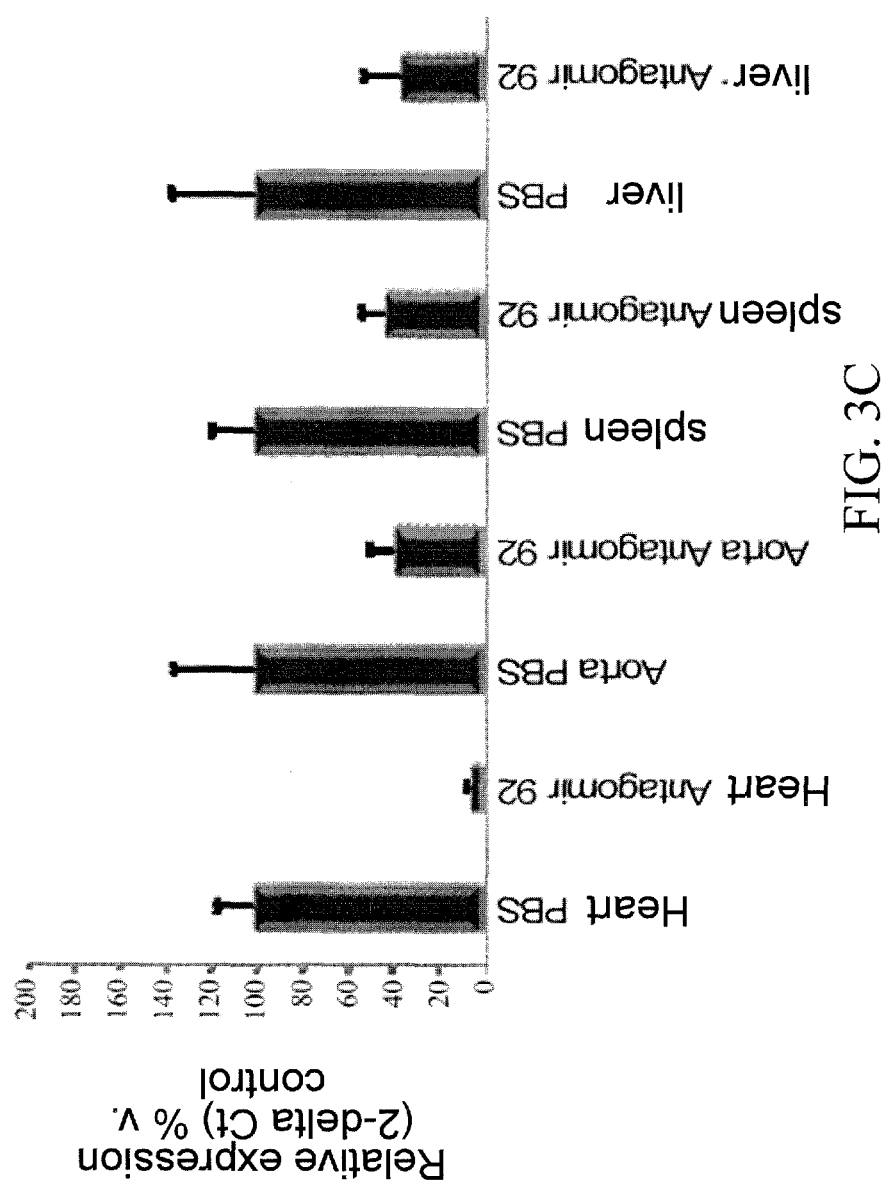
Figure 3D:
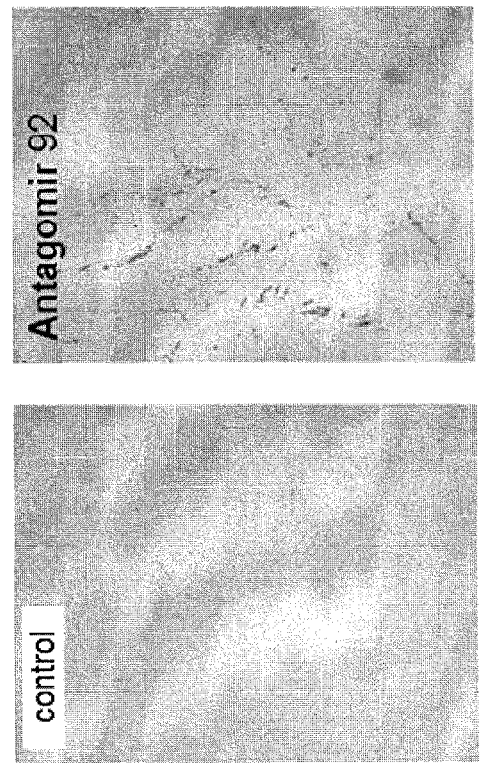
Figure 3E:
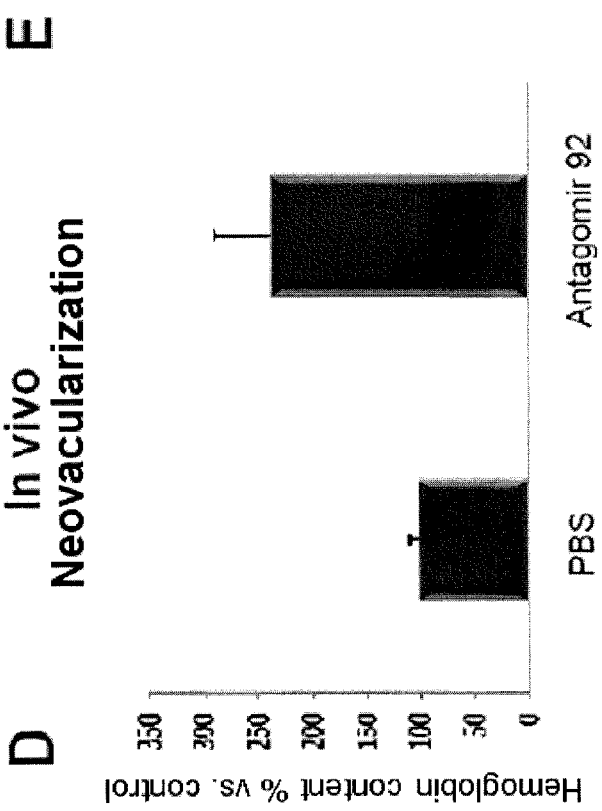

It was furthermore examined, whether the inhibition of miR-92 causes the stimulation of vessel growth. MiR-92 was inhibited by 2'-O-methyl antisense oligoribonucleotide (O-methyl-miR-92), and the formation of vessel structures in vitro was determined using a spheroid assay. O-methyl-miR-92 increases the sprout formation in vitro (FIG. 3A), which indicates that the inhibition of miR-92 could represent a new therapeutic strategy for improving the angiogenesis. In order to test this hypothesis, miR-92 was systemically inhibited using so-called "antagomirs", single-stranded RNA oligonucleotides, which, compared with specific miRNAs, have a complementary sequence. Chemical modifications lead to an increased stability, and cholesterol-conjugation to an improved uptake into the cells (15). Antagomirs directed against miR-92 were administered on three days, as depicted in FIG. 3B. The systemic administration of antagomirs improved the vessel growth and the perfusion of the "matrigel plug" in vivo (FIG. 3C/D). As a result, the inhibition of miR-92 increases endothelial cell functions in vitro and improves the vessel growth in vivo.

Identification of miR-92 Target-Genes

MiRNAs control target genes through a degradation of the target-mRNA or through translational repressions. In order to determine the target mRNAs that are degraded in response to miR-92 over-expression, a chip analysis with an Affymetrix mRNA gene expression array with 54.681 genes (HG-U133 Plus 2) was performed. The analysis of the regulated mRNAs identified different key enzymes that control the endothelial function, including eNOS, SIRT1, integrins, and growth factors, such as angeopoietin-2 (FIG. 4A). A fraction of the down-regulated genes is compatible with an analysis of potential miR-92 targets performed in silico (Table 1). In order to confirm the results of the screens, the protein expression of the respective genes was detected using Western blot or FACS analysis. In agreement with the results as predicted, the protein expression of eNOS, SIRT1 and Integrin a5 was significantly repressed by pre-miR-92 (FIG. 4B to 4E).

TABLE 1

In silico prediction of miR-92 target molecules mediating the biological effect of miR-92
miR-92 - Targets

| Integrin a5 |
| Integrin av |
| SIRT1 |
| MKK4 |
| KLF 2 |
| PCAF |
| EDG 1 |
| RAP 1B |

As a result, miR-92 exhibits a strong anti-angiogenic effect, and negatively influences endothelial cell functions in vitro and in vivo. In agreement with this, blocking of miR-92 by systemic infusion of an antagomir leads to an improved vessel growth in vivo. This result is surprising, since it is contrary to the pro-angiogenic activity of the miR-17-92 cluster as described (10).

The present data shows that miR-92 influences the expression of different proteins that are known to play a major role in the endothelial cell biology. Amongst the genes as identified using a microarray, in particular the down-regulation of eNOS, SIRT1, and integrin a5 on the protein level could be confirmed. Mice that are deficient for these proteins show an impaired vascular function and/or an impaired ability for postnatal neovascularization.

eNOS plays a role in the maintenance of vasoreactivity and blocks the apoptosis of endothelial cells (16). The histone deacetylase SIRT1 promotes the longevity in model organisms and controls neovascularization and vessel maturation in mammals (13, 17). The dysregulation of integrins can have a negative impact on the interaction with the cell matrix and thus impair anti-apoptotic signaling and cell migration (14, 18). The growth factor angiopoietin-2, its receptor Tie2, and protease inhibitors, such as TIMP4, control vessel maturation (19, 20). Accordingly, miR-92 interacts with a series of genes that control the endothelial cell functions at different levels. The ability of miR-92 to influence different effectors provides an advantage of the miRNA-based therapeutic strategy and helps to overcome the limited therapeutic capacity of a therapy of an ischemic disease based on a single growth factor or a single gene, since the complex processes of vessel growth, vessel maturation and the functional maintenance of vessels are known to require a finely tuned regulation of a series of genes.

As a result, the influencing of miR-92 represents a new therapeutic strategy for a control of endothelial cell functions. The systemic use of antagomirs as shown herein is particularly suitable for influencing of the miRNA functions. The inhibition of miR-92 by antagomirs increases vessel growth and contributes to an improvement of the neovascularization and vessel repair. With reference to the genes which are known for their atheroprotective effect, such as, for example, eNOS, the blockade of miR-92 is of use in the anti-atherosclerotic therapy. Since a neuroprotective role in neurodegenerative diseases (e.g. Morbus Parkinson) is also attributed to SIRT 1 (25), miR-92 antagomirs can be successfully used also in this disease scenario. In contrast to this, the over-expression of miR-92 is useful, for example for blocking tumor angiogenesis, since it strongly reduces vessel growth.

CITED LITERATURE

1 Carmeliet, P. (2000) Mechanisms of angiogenesis and arteriogenesis. *Nat Med* 6 (4), 389-395.
2 Adams, R. H. and Alitalo, K. (2007) Molecular regulation of angiogenesis and lymphangiogenesis. *Nat Rev Mol Cell Biol* 8 (6), 464-478
3 Bartel, D. P. (2004) MicroRNAs: genomics, biogenesis, mechanism, and function. *Cell* 116 (2), 281-297
4 Hofacker, I. L. (2007) How microRNAs choose their targets. *Nat Genet* 39 (10), 1191-1192
5 Yang, W. J. et al. (2005) Dicer is required for embryonic angiogenesis during mouse development. *J Biol Chem* 280 (10), 9330-9335
6 Suarez, Y. et al. (2007) Dicer dependent microRNAs regulate gene expression and functions in human endothelial cells. *Circ Res* 100 (8), 1164-1173
7 Kuehbacher, A. et al. (2007) Role of Dicer and Drosha for endothelial microRNA expression and angiogenesis. *Circ Res* 101 (1), 59-68
8 Poliseno, L. et al. (2006) MicroRNAs modulate the angiogenic properties of HUVECs. *Blood* 108 (9), 3068-3071
9 Venturini, L. et al. (2007) Expression of the miR-17-92 polycistron in chronic myeloid leukemia (CML) CD34+ cells. *Blood* 109 (10), 4399-4405
10 Dews, M. et al. (2006) Augmentation of tumor angiogenesis by a Myc-activated microRNA cluster. *Nat Genet* 38 (9), 1060-1065
11 Murohara, T. et al. (1998) Nitric oxide synthase modulates angiogenesis in response to tissue ischemia. *J Clin Invest* 101 (11), 2567-2578
12 Aicher, A. et al. (2003) Essential role of endothelial nitric oxide synthase for mobilization of stem and progenitor cells. *Nat Med* 9 (11), 1370-1376
13 Potente, M. et al. (2007) SIRT1 controls endothelial angiogenic functions during vascular growth. *Genes Dev* 21 (20), 2644-2658
14 Kim, S. et al. (2000) Regulation of integrin alpha vbeta 3-mediated endothelial cell migration and angiogenesis by integrin alpha5beta1 and protein kinase A. *J Biol Chem* 275 (43), 33920-33928.
15 Krutzfeldt, J. et al. (2005) Silencing of microRNAs in vivo with 'antagomirs'. *Nature* 438 (7068), 685-689
16 Dimmeler, S. and Zeiher, A. M. (1999) Nitric oxide—an endothelial cell survival factor. *Cell Death Differ* 6, 964-968
17 Imai, S. et al. (2000) Transcriptional silencing and longevity protein Sir2 is an NAD dependent histone deacetylase. *Nature* 403 (6771), 795-800.
18 Zhang, Z. et al. (1995) The alpha 5 beta 1 integrin supports survival of cells on fibronectin and up-regulates Bcl-2 expression. *Proc Natl Acad Sci USA* 92 (13), 6161-6165
19 Asahara, T. et al. (1998) Tie2 receptor ligands, Angiopoietin-1 and Angiopoietin-2, modulate VEGF-induced postnatal neovascularization. *Circ Res* 83, 233-240
20 Sang, Q. X. (1998) Complex role of matrix metalloproteinases in angiogenesis. *Cell Res* 8 (3), 171-177
21 Care, A. et al. (2007) MicroRNA-133 controls cardiac hypertrophy. *Nat Med* 13 (5), 613-618
22 Korff, T. and Augustin, H. G. (1998) Integration of endothelial cells in multicellular spheroids prevents apoptosis and induces differentiation. *J Cell Biol* 143 (5), 1341-1352
23 Diehl, F. et al. (2007) The histone methyltransferase MLL is an upstream regulator of endothelial cell sprout formation. *Blood* 109 (4), 1472-1478
24 Potente, M. et al. (2005) Involvement of FoxO transcription factors in angiogenesis and postnatal neovascularization. *J Clin Invest* 115(9), 2382-2392.
25 Dillin, A. and Kelly, J. W. (2007) The yin-yang of sirtuins. *Science* 317 (5837), 461-462.

---

We claim:

1. A method for inhibiting neovascularization wherein the method comprises reducing expression of endothelial nitric oxide synthase (eNOS), sirtuin 1 (SIRT1), integrin alpha 5, or a combination thereof in an endothelial cell, wherein the reducing comprises increasing the expression of miR-92a in the endothelial cell by introducing into the endothelial cell a miR-92a construct, wherein said construct comprises an expressible miR-92a sequence, wherein the expressible miR-92a sequence comprises a sequence according to SEQ ID NO: 1, 2 or 4, whereby the reduction in the expression of eNOS, SIRT1, integrin alpha 5, or a combination thereof in the endothelial cell inhibits neovascularization.

2. The method of claim 1, wherein the expressible miR-92a sequence is functionally linked to a promoter.

* * * * *